United States Patent
Romasn-Hess et al.

(10) Patent No.: US 6,855,434 B2
(45) Date of Patent: Feb. 15, 2005

(54) IONIC SUPERABSORBENT POLYMERS WITH ENHANCED SWELLING CHARACTERISTICS

(75) Inventors: Alice Y. Romasn-Hess, Pinehurst, NC (US); Joseph R. Feldkamp, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 247 days.

(21) Appl. No.: 10/084,571

(22) Filed: Feb. 27, 2002

(65) Prior Publication Data

US 2003/0162869 A1 Aug. 28, 2003

(51) Int. Cl.⁷ .......................... B32B 27/00; C08K 5/42; A61F 13/15
(52) U.S. Cl. ................... 428/474.4; 428/500; 523/105; 524/157; 524/238; 604/358
(58) Field of Search .............................. 428/474.4, 500; 523/105; 604/358

(56) References Cited

U.S. PATENT DOCUMENTS

| | | |
|---|---|---|
| 5,300,192 A | 4/1994 | Hansen et al. |
| 5,308,896 A | 5/1994 | Hansen et al. |
| 5,352,480 A | 10/1994 | Hansen et al. |
| 5,998,032 A * | 12/1999 | Hansen et al. ............... 428/403 |
| 6,080,806 A | 6/2000 | Bett et al. |
| 6,395,395 B1 | 5/2002 | Hansen et al. |
| 6,639,120 B1 * | 10/2003 | Wallajapet et al. ......... 604/368 |

FOREIGN PATENT DOCUMENTS

| | | |
|---|---|---|
| EP | 0 637 594 A2 | 2/1995 |
| WO | WO 95/19191 | 7/1995 |
| WO | WO 96/31644 A1 | 10/1996 |
| WO | WO 99/30751 A2 | 6/1999 |

OTHER PUBLICATIONS

Öztop, et al., Influence of Some Aromatic Amino Acids on the Swelling Behavior of Acrylamide/Maleic Acid Hydrogel, Polymer Bulletin, 1998, 40:575–581.

International Search Report from PCT/US03/02267 dated Aug. 18, 2003.

* cited by examiner

Primary Examiner—Kriellion A. Sanders
(74) Attorney, Agent, or Firm—Senniger Powers (57) ABSTRACT

Ionic superabsorbent polymers having increased swelling capacity of salt-containing solutions are disclosed. The ionic superabsorbent polymers of the present invention contain an additive to increase the osmotic activity of the polymer in the presence of a salt-containing solution. The additive used in combination with the ionic superabsorbent polymer is capable of forming a zwitterion at a pH of from about 1 to about 9, has a dipole moment greater than that of water, and has a molecular weight less than about 10,000 grams/mole.

33 Claims, 4 Drawing Sheets

IONIC SUPERABSORBENT POLYMERS WITH ENHANCED SWELLING CHARACTERISTICS

BACKGROUND OF THE INVENTION

The present invention relates to superabsorbent polymers having enhanced swelling characteristics. More particularly, the present invention relates to an absorbent composition comprising an ionic superabsorbent polymer material and an absorbency-enhancing additive having a dipole moment greater than water which significantly increases the swelling characteristics of ionic superabsorbent polymers in the presence of salt-containing solutions such as urine, menses, blood and other body exudates.

The use of superabsorbent polymers such as ionic superabsorbent polymers is standard throughout the absorbent products industry. The absorbent core of many absorbent articles, such as diapers, sanitary napkins, training pants, and incontinence products, is typically comprised of one or more layers of cellulose fluff pulp, intermixed with superabsorbent polymers. Other layers are often used in combination with the absorbent core depending upon the intended application of the product.

Ionic superabsorbent polymers, also commonly referred to as ionic hydrogels or ionic hydrocolloids, are typically cross-linked ionic polymers that are able to absorb an amount of pure water equal to at least ten times their dry weight and retain the pure water under a moderate external pressure. Ionic superabsorbent polymers can be anionic in nature (e.g., acrylate based or sulfonate based), or can be cationic in nature (e.g., a partly neutralized polyamine), and as such can either have positive or negative charges along the backbone of the polymer structure. Ionic superabsorbent polymers are electrically charged in solution because various groups attached to the polymer chain easily become ionic. Examples of groups which can become electrically charged in ionic superabsorbent polymers include carboxylate groups and amine groups.

Liquid absorbed by a superabsorbent polymer is taken directly into the molecular structure itself, and is not simply contained in pores or openings in the material from which it could be easily expressed by the application of pressure. The preferred commercially available ionic superabsorbent polymers are generally crosslinked polyacrylates such as poly(acrylic acid) or acrylic acid grafted onto starch. The carboxyl functionality on the polymer backbone is partially neutralized with sodium or potassium hydroxide. Some ionic superabsorbent polymers are formed by graft polymerizing acrylonitrile onto gelatinized starch followed by hydrolysis of the polyacrylonitrile to poly(acrylic acid-co-acrylamide).

Although ionic superabsorbent polymers have the ability to absorb many times their weight of pure water, when contacted with aqueous salt solutions, their ability to effectively absorb liquid is generally reduced by more than a factor of five, or even more, depending upon the ionic strength of the salt solution. The degradation of absorption capacity suffered by ionic polymers in salt solutions is believed to be due to a collapse of the counterion atmosphere surrounding the ionic backbone of the polymer chains. The counterion atmosphere is made up of ions of opposite charge to the charges along the backbone of the ionic polymer and are present in the salt solution (e.g., sodium or potassium cations surrounding the carboxylate anions distributed along the backbone of a polyacrylate anionic polymer). As the concentration of ions in the salt solution contacting the superabsorbent ionic polymer increases, the ion concentration gradient in the liquid phase from the exterior to the interior of the polymer begins to decrease and the counterion atmosphere thickness, typically referred to as the Debye thickness, can be reduced from about 20 nanometers (in pure water) to about 1 nanometer or less. When the counterion atmosphere is highly extended (i.e., not significantly collapsed around the polymer backbone as when pure water is absorbed), the counterions are much more osmotically active and therefore promote a much higher degree of liquid absorbency. However, when the ion concentration in the absorbed liquid increases, the counterion atmosphere collapses and absorption capacity is diminished.

Hansen et al., in U.S. Pat. No. 5,998,032, disclose a process for enhancing the blood absorbence properties of superabsorbent materials by combining an enhancing agent with the superabsorbent particles. The enhancing agent includes functionalities that allow the enhancing agent to hydrogen bond to the superabsorbent material. A suitable enhancing agent, such as glycine, is present in an amount up to 10% of the total weight of the superabsorbent material and enhancing agent. Although Hansen et al. do disclose a slight improvement in the blood absorbent properties of superabsorbent materials, a need continues to exist in the art for improved superabsorbent materials capable of absorbing increased amounts of salt-containing body exudates.

SUMMARY OF THE INVENTION

The present invention is directed to absorbent compositions comprising an ionic superabsorbent polymer material which exhibit improved absorption characteristics when contacted with aqueous salt-containing solutions. Specifically, the absorbent compositions of the present invention comprise an anionic and/or cationic cross-linked superabsorbent polymer material and an absorbency-enhancing additive which increases the osmotic activity, and hence the swelling capacity, of the ionic superabsorbent polymer material when contacted with aqueous salt solutions. It is believed that the absorbency-enhancing additive is caused to partition from the liquid phase into the interior of the ionic superabsorbent polymer material to the extent that a positive excess mole fraction of absorbency-enhancing additive accumulates and persists in the interior of the ionic superabsorbent polymer material as compared to the liquid phase of the system. This positive excess mole fraction results in a concentration gradient of absorbency-enhancing additive from the exterior liquid phase (reduced content) to the interior of the polymer material (increased content) and causes the polymer material to become osmotically active, thereby promoting further substantial absorption of liquid into the interior of the ionic superabsorbent polymer.

In order to achieve the above-described partitioning effect, the absorbency-enhancing additive combined with the ionic superabsorbent polymer material possesses a unique combination of characteristics. The absorbency-enhancing additive is capable of forming a zwitterion in the aqueous salt-containing solution over a wide pH range of from about 1 to about 9. Along with its zwitterion-forming properties, the absorbency-enhancing additive has a dipole moment greater than about 1.85 Debye (the dipole moment of water), and a molecular weight of less than about 10,000 grams/mole to ensure the absorbency-enhancing additive can enter into the polymer matrix without substantial steric hindrance problems. Furthermore, the absorbency-enhancing additive is combined with an ionic superabsorbent polymer such that the weight ratio of ionic superabsorbent polymer to absorbency-enhancing additive is at least about 1:1, and preferably at least about 1:2 so that there is at least an equal amount of absorbency-enhancing additive and ionic superabsorbent polymer. The ionic superabsorbent polymers can be cationic or anionic in nature, and when combined with the absorbency-enhancing additive described herein, can typically absorb at least about 10 times their dry weight of an aqueous salt solution, such as urine.

Briefly, therefore, the present invention is directed to an absorbent composition for absorbing an aqueous salt solution such as urine. The composition comprises an ionic superabsorbent polymer material and an absorbency-enhancing additive in a weight ratio of at least about 1:1. The absorbency-enhancing additive has a dipole moment greater than about 1.85 Debye, a molecular weight of no more than about 10,000 grams/mole and is capable of forming a zwitterion in the aqueous salt solution at a pH of from about 1 to about 9.

In a preferred embodiment, the ionic superabsorbent polymer material comprises poly(acrylic acid), the absorbency-enhancing additive has a dipole moment of at least about 10 Debye, a molecular weight of no more than about 1000 grams/mole, and the weight ratio of poly(acrylic acid) to absorbency-enhancing additive is at least about 1:2.

The invention is further directed to a process for increasing the osmotic activity of an ionic superabsorbent polymer in the presence of an aqueous salt solution. The process comprises combining an absorbency-enhancing additive with the ionic superabsorbent polymer prior to contacting the ionic superabsorbent polymer with the aqueous salt solution. The weight ratio of ionic superabsorbent polymer to absorbency-enhancing additive is at least about 1:2. The absorbency-enhancing additive has a dipole moment greater than about 1.85 Debye, a molecular weight of no more than about 10,000 grams/mole and is capable of forming a zwitterion in the aqueous salt solution at a pH of from about 1 to about 9.

In a further embodiment of the present invention, the absorbent composition comprising the ionic superabsorbent polymer and absorbency-enhancing additive is combined with fluff fiber in an absorbent product.

Other objects and features of this invention will be in part apparent and in part pointed out hereinafter.

DETAILED DESCRIPTION OF THE PREFERRED EMBODIMENTS

In accordance with the present invention, the swelling capacity of ionic superabsorbent polymers in the presence of salt-containing solutions is significantly enhanced by an absorbency-enhancing additive. More specifically, it has been discovered that the absorption capacity of ionic superabsorbent polymer materials when contacted with salt-containing solutions is markedly improved by the presence of a sufficient amount of absorbency-enhancing additive having a dipole moment greater than water and capable of forming a zwitterion over a wide pH range. It is believed that such absorbency-enhancing additives tend to accumulate in the interior of the ionic superabsorbent polymer and counteract the decrease in osmotic activity typically experienced by ionic superabsorbent polymers when used to absorb salt-containing solutions such as urine and other biological liquids.

The absorbent composition of the present invention comprises an ionic superabsorbent polymer material (i.e., superabsorbent polymers containing backbones that are easily ionized) and the absorbency-enhancing additive. Preferably, the absorbency-enhancing additive is combined with the ionic superabsorbent polymer. The ionic superabsorbent polymer materials suitable for use in combination with the absorbency-enhancing additives described herein include both cationic and anionic superabsorbent polymers. As used herein, the term "ionic superabsorbent polymer" is meant to include cross-linked ionic polymers which are able to absorb an amount of pure water equal to at least about ten times their dry weight. Ionic polymers are also referred to in the art as ionic hydrogels or ionic hydrocolloids. The ionic superabsorbent polymers of the present invention are preferably cross-linked polymers as cross-linking prevents the polymer chains from significantly dissolving into the surrounding aqueous medium and allows the polymer to be a separate phase apart from the aqueous medium. Examples of anionic superabsorbent polymers include, for example acrylate based or sulfonate based polymers. Particularly preferred anionic superabsorbent polymers include polyacrylates, with poly(acrylic acid) being particularly preferred. An example of a cationic superabsorbent polymer is a partly neutralized polyamine such as a polyallyl amine. The counterions of the ionic superabsorbent polymers of the present invention are not critical and can include, for example, sodium, potassium, and lithium for anionic superabsorbent polymers, and chloride or bromide counterions for cationic superabsorbent polymers.

In accordance with the present invention, it is preferred that the ionic superabsorbent polymers used in combination with the absorbency-enhancing additives described herein have a degree of ionization in aqueous salt solutions of at least about 10% to aid in the accumulation of the absorbency-enhancing additive in the interior of the ionic superabsorbent polymer as discussed below. Preferably, the degree of ionization of the ionic superabsorbent polymers is at least about 20%, more preferably at least about 40%, and still more preferably from at least about 50% to 80% or more. As discussed more fully below, the electric field of the ionized superabsorbent polymer plays a significant role in the collection and partition of the absorbency-enhancing additives described herein in the interior of the polymer which results in increased osmotic activity of the ionic superabsorbent polymer in the presence of salt solutions.

The absorbency-enhancing additive combined with the ionic superabsorbent polymer material is capable of forming a zwitterion in salt-containing aqueous solutions at a pH of from about 1 to about 9. That is, both a positive and a negative charge form on a molecule of the absorbency-enhancing additive when in solution. When a zwitterion is formed in this pH range, the acidic group neutralizes the basic group of the same molecule resulting in a dipolar molecule having separately positive and negative charges on the molecule. The dipolar nature of the absorbency-enhancing additives described herein aids in the accumulation of the absorbency-enhancing additive into the interior of the ionic superabsorbent polymer when in contact with a aqueous salt solution.

The absorbency-enhancing additive combined with the ionic superabsorbent polymer material preferably has a dipole moment greater than that of water. As used herein, dipole moments refer to dipole moments measured in the vapor state. The dipole moment of water in the vapor state is 1.85 Debye. Accordingly, the dipole moment of the absorbency-enhancing additive is preferably greater than about 1.85 Debye. In a more preferred embodiment, the dipole moment of the absorbency-enhancing additive is at least about 2 Debye, even more preferably at least about 5 Debye, and most preferably at least about 10 Debye or more to increase the absorbency-enhancing additive's ability to penetrate into the interior of the ionic superabsorbent polymer. As the dipole moment of the absorbency-enhancing additive increases, as compared to the water present in the solution, the absorbency-enhancing additive has a greater affinity toward the highly charged backbone of the ionic superabsorbent polymer and begins to substantially replace water molecules in this area as discussed below. This replacement leads to the partition and accumulation effects described herein which ultimately results in increased osmotic activity and swelling capacity of the ionic superabsorbent polymer.

As mentioned above, ionic superabsorbent polymers such as sodium polyacrylate are ionized polyacids with the charged, cross-linked polymer chains surrounded by an atmosphere of counterions (sodium ions in the case of sodium polyacrylate) to render the overall charge of the molecule neutral. The strong electric field associated with the ion atmosphere provides the basis for accumulation of the absorbency-enhancing additive having a high dipole moment within the interior of the ionic superabsorbent polymer. Based on free energy considerations, the absorbency-enhancing additive, which is more polar than water, in the solution is highly favored in the ionic superabsorbent polymer's interior where the electric field is strongest. The thermodynamic energy of the overall system (ionic superabsorbent polymer and aqueous salt solution) is reduced if the liquid inside of the ionic polymer can develop a higher dielectric constant by shifting or redistributing components of the system. A higher dielectric constant leads to lower energy in the system as the work involved in creating charges on the polymer backbone, along with its corresponding counterions, is reduced.

In the systems described herein comprising an ionic superabsorbent polymer material in contact with an aqueous salt solution, a higher dielectric constant can be achieved if the more polar zwitterions described above accumulate within the ionic superabsorbent polymer material to a higher concentration than that found in the solution outside of the ionic superabsorbent polymer. This accumulation or partitioning of the highly polar absorbency-enhancing additives into the interior of the ionic superabsorbent polymer results in the development of a positive excess mole fraction of the absorbency-enhancing additive in the interior of the ionic superabsorbent polymer as compared to the liquid portion of the system which becomes depleted of absorbency-enhancing additive and hence has a reduced mole fraction of absorbency-enhancing additive. The positive excess mole fraction of absorbency-enhancing additive in the interior of the ionic superabsorbent polymer causes a concentration gradient of absorbency-enhancing additive to form between the external liquid portion of the system and the interior of the ionic superabsorbent polymer which in turn causes the ionic superabsorbent polymer material to become osmotically active and draw liquid toward it thereby promoting further substantial absorption of liquid by the ionic superabsorbent polymer.

In accordance with the present invention, the absorbency-enhancing additives for combining with the ionic superabsorbent polymers of the present invention preferably have a molecular weight such that the absorbency-enhancing additive can be easily partitioned and enter into the interior of the ionic superabsorbent polymer matrix. If the molecular weight of the compound is too high, steric hindrance may prevent the absorbency-enhancing additive from penetrating into the interior of the polymer structure to a sufficient extent. Preferably, the absorbency-enhancing additives have a molecular weight of no more than about 10,000 grams/mole, more preferably no more than about 5,000 grams/mole, even more preferably no more than about 1,000 grams/mole, still more preferably no more than about 500 grams/mole, still more preferably no more than about 150 grams/mole, and even more preferably no more than about 100 grams/mole to allow easy penetration into the interior of the ionic superabsorbent polymer.

Representative examples of absorbency-enhancing additives include amino acids and sulfonic acid and phosphonic acid analogs of amino acids. More specifically, suitable absorbency-enhancing additives include glycine (dipole moment=12.8 Debye), alpha-alanine (dipole moment=12.6 Debye), beta-alanine (dipole moment=14.6 Debye), betaine, and taurine. A particularly preferred absorbency-enhancing additive is glycine. However, it should be understood that other absorbency-enhancing additives, including other amino acids and derivatives thereof having the characteristics described herein, may be used in the practice of the present invention.

The amount of absorbency-enhancing additive added to the ionic superabsorbent polymer should produce an aqueous concentration of absorbency-enhancing additive sufficient to produce significant additional absorbency by the ionic superabsorbent polymer once the absorbency-enhancing additive accumulates in the interior of the ionic superabsorbent polymer after contacting and dissolving into the aqueous salt solution. The amount of absorbency-enhancing additive combined with the ionic superabsorbent polymer to produce an aqueous salt solution sufficient to improve osmotic activity in the ionic superabsorbent polymer is typically a mole fraction (of the aqueous solution) of at least about 0.01, and more preferably at least about 0.02. By using the molecular weight of the absorbency-enhancing additive and assuming one total mole of absorbency-enhancing additive and water, the weight percent of the aqueous solution which comprises the absorbency-enhancing additive can be calculated. For example, if glycine (molecular weight 75.07 grams/mole) is the absorbency-enhancing additive, the amount of glycine to be combined with the ionic superabsorbent polymer to achieve the desired mole fraction of glycine can be calculated by first calculating the weight percent of glycine required (based on one mole of aqueous solution comprising water and glycine):

0.02 moles of glycine×75.07 grams/mole=1.501 grams of glycine 0.98 moles of water×18 grams/mole=17.640 grams of water 1.501/1.501+17.640=0.078×100=7.84% (by weight) glycine in solution.

If, for example, it is assumed that the insult to the absorbent article comprising the ionic superabsorbent polymer and the absorbency-enhancing additive is 30.0 grams liquid per gram of dry ionic superabsorbent polymer, the amount of glycine (in grams) that should be incorporated into 1 gram of ionic superabsorbent polymer to achieve a mole fraction of glycine of 0.2 in the liquid system can be calculated as follows:

0.078×30 grams=2.34 grams of glycine per gram of ionic superabsorbent.

Based on these calculations, a suitable weight ratio of ionic superabsorbent polymer to glycine in the absorbent composition would be about 1:2. In accordance with the present invention, the ionic superabsorbent polymer material is combined with an amount of absorbency-enhancing additive at least equal (by weight) to the amount of superabsorbent polymer; that is, there is at least as much absorbency-enhancing additive present as ionic superabsorbent polymer. This amount of absorbency-enhancing additive ensures sufficient partitioning of the absorbency-enhancing additive into the ionic superabsorbent polymer and has been discovered to provide a significant absorbency increase. For example, a weight ratio of ionic superabsorbent polymer to glycine (or similar compounds) is preferably at least about 1:1, and more preferably at least about 1:2. Weight ratios of superabsorbent polymers to absorbency-enhancing additives can also be 1:3, 1:4, or even 1:5 or greater depending upon the absorbency-enhancing additive in accordance with the present invention. One skilled in the art will recognize that suitable amounts of other compounds useable as absorbency-enhancing additives in accordance with present invention can be calculated in a manner similar to the above calculations.

As discussed herein, the absorbency-enhancing additive is combined with the ionic superabsorbent polymer prior to contacting the salt-containing solution to produce the absorbent composition of the present invention. In some methods of combining the absorbency-enhancing additive with the ionic superabsorbent polymer, the absorbency-enhancing additive will be incorporated directly into the polymer matrix. In other methods of combining the absorbency-enhancing additive with the ionic superabsorbent polymer, the absorbency-enhancing additive will be incorporated onto the surface of the ionic superabsorbent polymer, but not necessarily into the matrix of the polymer. Regardless of whether the absorbency-enhancing additive is initially introduced into the interior of the ionic superabsorbent polymer or onto the surface of the polymer, once the ionic superabsorbent polymer is contacted with the liquid phase of the system, the absorbency-enhancing additive dissolves into the liquid and begins to redistribute or partition into the interior of the ionic superabsorbent polymer.

In one embodiment, the absorbency-enhancing additive is combined with the ionic superabsorbent polymer material in a batch-type process utilizing a fluidized bed system held in a sealed chamber. A known amount of ionic superabsorbent polymer granules, particles, fibers or other suitable polymer form, are suspended in the fluidized bed (e.g., using air as the suspending gas) while an aqueous solution containing a known amount of absorbency-enhancing additive is introduced into the chamber over the granules in the form of a fine spray. Water is evaporated from the aqueous solution, depositing a layer of the absorbency-enhancing additive onto the granules. Typically, the suspending gas in the sealed chamber is maintained at an elevated temperature of, for example, about 93° C. in order to more quickly evaporate the water in which the absorbency-enhancing additive is dissolved. As the process continues and the fine spray is introduced into the chamber containing the ionic superabsorbent polymer granules, a coating comprising the absorbency-enhancing additive is built up on the outside of the granules until the desired absorbency-enhancing additive to ionic superabsorbent polymer weight ratio is realized.

For example, glycine can be introduced onto ionic superabsorbent polymer granules using the fluidized bed system described above to achieve a suitable weight ratio of ionic superabsorbent polymer to glycine of 1:2 as follows: an aqueous solution of glycine is prepared by dissolving 180 grams of glycine into 1000 mL of water. The temperature of the water may be increased to improve the dissolution rate of the glycine. Once the glycine is fully dissolved, the 18% (by weight) glycine solution is introduced as a fine spray as described above onto about 90 grams of ionic superabsorbent polymer in suspended state in the fluidized bed reactor to combine the glycine and the polymer material. The fine spray is continuously introduced over the particles until all of the water has been evaporated leaving a coating of about 180 grams glycine (minus a small amount which may have coated the chamber) on the 90 grams of polymer resulting in about a 1:2 polymer to absorbency-enhancing additive weight ratio.

Once the desired weight ratio of absorbency-enhancing additive to ionic superabsorbent polymer is reached, verification of the coating thickness and uniformity can be conducted through direct examination of the particles under a microscope. This method produces absorbency-enhancing additive-coated ionic superabsorbent polymer particles. When the coated particles are utilized in absorbent products and contacted with the liquid salt-containing insult, the coating comprising the absorbency-enhancing additive dissolves into the liquid and redistributes into the interior of the ionic superabsorbent polymer as described herein.

In an alternative embodiment, the absorbency-enhancing additive can be incorporated into the polymer matrix instead of being coated onto the polymer surface. In this embodiment, the absorbency-enhancing additive is first dissolved into water at a suitable concentration. In the case of glycine as the absorbency-enhancing additive, the concentration of absorbency-enhancing additive is suitably 25% by weight. The temperature is increased, as necessary, to dissolve the absorbency-enhancing additive. Once the absorbency-enhancing additive is dissolved, the liquid mixture is contacted with an ionic superabsorbent polymer material. If glycine is utilized, a suitable weight ratio of ionic superabsorbent polymer to glycine is, for example, 1:2. Such a weight ratio would result in a liquid to ionic superabsorbent polymer weight ratio of 8:1 and a water to ionic superabsorbent polymer weight ratio of 6:1. Once the ionic superabsorbent polymer imbibes all of the liquid, the swollen ionic superabsorbent polymer is spread out onto a hard surface to a depth of a few centimeters and dried. The drying process can occur at room temperature, or may be completed at an elevated temperature of, for example, at about 65° C. to decrease drying time. The result is an ionic superabsorbent polymer which contains the absorbency-enhancing additive inside of the polymer matrix.

In another embodiment, the absorbency-enhancing additives described herein can be incorporated into an ionic superabsorbent polymer by mixing the absorbency-enhancing additive, in powder form, with powderous ionic superabsorbent polymers. The mixture is thoroughly agitated and then can be incorporated directly into an absorbent product in accordance with the present invention. Once the absorbent product is insulted during use, the absorbency-enhancing additive will dissolve into the liquid and migrate toward the interior of the ionic superabsorbent polymer and increase its swelling capacity as described herein. When the absorbency-enhancing additive is glycine, a suitable weight ratio of ionic superabsorbent polymer to glycine is, for example, 1:2.

In a still further embodiment, the absorbency-enhancing additives described herein can be spray coated directly onto an absorbent article comprising an ionic superabsorbent polymer. In spray coating, the absorbency-enhancing additive described herein is first thoroughly mixed with a substantially body fluid-soluble or body fluid-dispersable adhesive agent to disperse the absorbency-enhancing additive throughout the adhesive material. The adhesive material can comprise a body fluid-soluble adhesive which will partially or completely dissolve upon insult by the wearer and allow release of the absorbency-enhancing additive, or may be comprised of a material which disperses upon insult allowing release of the absorbency-enhancing additive. Suitable body fluid-soluble adhesives include, for example, polyvinyl pyrrolidone and polyvinyl alcohol, and combinations thereof. After the adhesive and absorbency-enhancing additive are thoroughly mixed, they can be applied by, for example, spraying, knifing, or roller coating, onto the desired area of the product comprising the ionic superabsorbent polymer. The adhesive-absorbency-enhancing additive mixture adheres to the product where it is stable until insult occurs by the wearer. Upon insult, the adhesive releases the absorbency-enhancing additive such that it may dissolve in the body fluid and partition into the matrix of the ionic superabsorbent polymer.

In another embodiment, the absorbent compositions comprising the ionic superabsorbent polymer and absorbency-enhancing additive can further include fluff fibers. Fluff or filler materials are well-known in the art, and may include, for example, cellulosic fluff such as wood pulp fluff. One suitable type of wood pulp fluff is identified with the trade designation CR1654, (U.S. Alliance, Childersburg, Ala.), and is a bleached, highly absorbent sulfate wood pulp containing primarily soft wood fibers. However, the wood pulp fluff can be exchanged with other hydrophilic fiber materials, such as synthetic, polymeric, or meltblown fibers or with a combination of meltblown fibers and natural fibers. Typically, the composite product comprises from about 5% (by weight) to about 99% (by weight) of the absorbent composition and from about 1% (by weight) to about 95% (by weight) fluff fibers.

In a further embodiment, the additive, such as glycine, can be coated onto a superabsorbent particle as described herein, and the glycine coated superabsorbent particle bound to other fibers, such as cellulosic fibers or other fluff fibers as described above, within the absorbent core to stabilize the coated superabsorbent particles in a particular area of the absorbent core. In this embodiment, no spray binder to attach the particles to the absorbent core fibers is required as the glycine coating functions as a binder material, as well as an enhancing agent once it is wetted. The glycine attaches the glycine-coated superabsorbent particles to the absorbent core fibers, and forms a bond resistant to mechanical disruption. Upon being contacted by fluid, the glycine then acts as an absorbency-enhancing agent as described herein.

In a less preferred embodiment of the present invention, the absorbency-enhancing additive as described herein can be introduced in powdered form into a composite absorbent product comprising an ionic superabsorbent polymer material and fluff or filler material, or other materials, but the absorbency-enhancing additive is neither incorporated into or onto the ionic superabsorbent polymer. That is, the absorbency-enhancing additive is introduced separate and apart from the ionic superabsorbent polymer material into the composite product. Once the absorbent product is insulted, the absorbency-enhancing additive can dissolve into the insult liquid and partition into the ionic superabsorbent polymer material.

When a product comprising fluff fiber, ionic superabsorbent polymer material, and absorbency-enhancing additive is contacted with an aqueous salt solution, the absorbency-enhancing additive dissolves into the solution and migrates to the ionic superabsorbent polymer such that the partitioning effect described above occurs to increase the osmotic activity of the ionic superabsorbent polymer material. Based on the disclosure herein, one skilled in the art would recognize that the absorbency-enhancing additive could also be introduced into or onto the fluff fibers or other fibrous material incorporated into an absorbent article which also comprises an ionic superabsorbent polymer material. One skilled in the art will also recognize that the absorbency-enhancing additive described herein for use in combination with an ionic superabsorbent polymer could be introduced into an absorbent product by combining the absorbency-enhancing additive with any one of a number of various layers of an absorbent product which, when insulted, would allow the absorbency-enhancing additive to dissolve therein and partition into the ionic superabsorbent polymer material. For example, the absorbency-enhancing additive could be introduced into a surge layer, wicking layer, or pervious liner layer.

The absorbent compositions of the present invention comprising an ionic superabsorbent polymer and absorbency-enhancing additive capable of improving the absorbency of the polymer in salt-containing solutions can be incorporated into numerous absorbent products in accordance with the present invention. These products include, for example, diapers, training pants, tampons, feminine napkins, interlabial pads, wound management products, and adult incontinence garments.

The absorbent compositions including an absorbent enhancing additive are capable of absorbing at least about 10, 12, or even 14 times their dry weight of a salt-containing solution. As used herein, the term "salt solution" or "salt-containing solution" is meant to refer to aqueous solutions which contain sodium chloride, potassium chloride and/or other salts and behave similarly to an aqueous sodium chloride solution having a concentration of from about 0.2% (by weight sodium chloride) to about 5% (by weight sodium chloride). For example, human urine typically contains about 0.9% (by weight) salts and thus would fall within the definition of the terms "salt solution" or "salt-containing solution" as used herein. Also, other common bodily fluids such as menses, blood, blood-plasma mixtures, and wound excretions are included in the definition and are within the scope of the present invention.

The present invention is illustrated by the following examples which are merely for the purpose of illustration and are not to be regarded as limiting the scope of the invention or manner in which it may be practiced.

EXAMPLE 1

In this Example, the effect of combining glycine with an ionic superabsorbent polymer on the absorption capacity of the ionic superabsorbent polymer in a salt-containing solution was analyzed.

Nine separate saline solutions (100 g of 0.9% saline) containing various amounts of glycine were prepared in different 100 mL graduated cylinders. The mole fraction of glycine (Aldrich Chemical, Milwaukee, Wis.) in the saline solutions was varied in the nine samples as follows: 0, 0.001, 0.002, 0.004, 0.006, 0.008, 0.010, 0.014, and 0.02. For example, this corresponds to a weight ratio of superabsorbent polymer to glycine of about 1:4 for the 0.01 glycine solution and a weight ratio of superabsorbent polymer to glycine of about 1:8 for the 0.02 glycine solution. Each sample had a pH of about 5.5. Sodium polyacrylate ionic superabsorbent polymer (1 g of FAVOR 880, Stockhausen Inc., Greensboro, N.C.) was introduced into a dry 100 mL graduated cylinder and the graduated cylinder filled with a sample saline solution up to 100 mL. The FAVOR 880, which remained on the bottom of the graduated cylinder, was permitted to swell freely for 60 minutes in each saline solution sample. After the time period for swelling had ended, the swelled volume of the Favor 880 polymer in each saline solution sample was determined visually.

Figure 1:
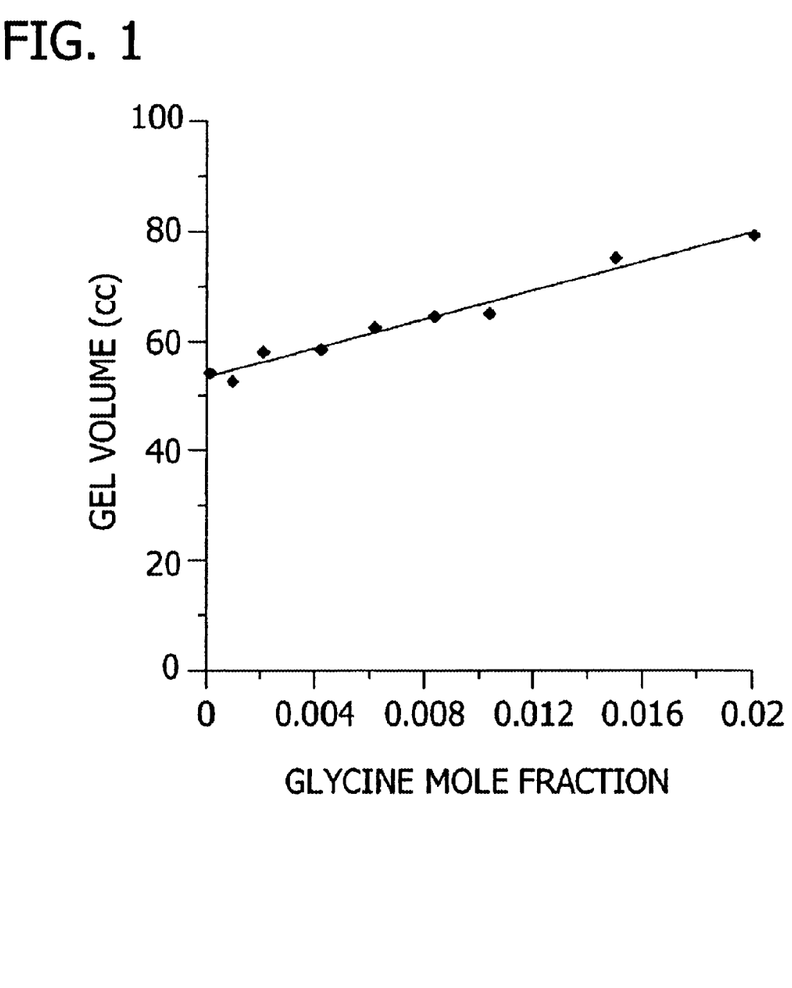
FIG. 1 is a graph showing the effect of glycine on the swelling of an anionic superabsorbent polymer in the presence of saline solution.

FIG. 1 shows the effect of glycine on the swelling of the ionic superabsorbent polymer and hence the absorption of the liquid. As illustrated, the introduction of glycine into the saline solution, and ultimately into the ionic superabsorbent polymer, resulted in increased swelling of the ionic superabsorbent polymer. The ionic superabsorbent polymer volume at equilibrium increased nearly linearly with increasing glycine concentration in the saline solution. At a mole fraction of glycine of zero, the ionic superabsorbent polymer absorbed a volume of about 54 cc of liquid while at a mole fraction of glycine of about 0.02, the ionic superabsorbent polymer absorbed a volume of about 79 cc. This equates to an increase in swelled volume of the ionic superabsorbent polymer of about 46%.

EXAMPLE 2

In this Example, ionic superabsorbent polymers combined with glycine were evaluated for absorbency under a load of about 2.0 kPa.

Ionic superabsorbent polymers are often utilized in situations where the swelling of the ionic superabsorbent polymer is restricted due to externally applied loads. To assess the effect of loading on any enhancement in swelling due to the introduction of glycine into an ionic superabsorbent polymer, swelling capacity under a load of 2.0 kPa was evaluated at two different levels of aqueous saline solution.

Six samples were prepared and analyzed in this Example. The first three samples comprised 0.9% (by weight) sodium chloride and 0.0% (by weight) glycine, 4.0% (by weight) glycine, and 8.0% (by weight) glycine, respectively. The last three samples were identical to the first three samples with the exception that the weight percent of sodium chloride was 1.8%. About 40 mL of each sample was prepared and introduced into a Petrie dish having a diameter of about 10 cm nd a depth of about 3 cm.

Ionic superabsorbent polymer (0.160 g of FAVOR 880 Stockhausen Inc., Greensboro, N.C.) was introduced into a small cylindrical chamber resting on a fine screen so that the ionic superabsorbent polymer rested on top of the screen but did not pass through it. The cylindrical chamber/ionic superabsorbent polymer/fine screen assembly was weighed and then set in a Petrie dish containing a saline solution sample such that the ionic superabsorbent polymer could draw the liquid through the screen and absorb it. Then, water was introduced into the cylindrical chamber on top of the ionic superabsorbent polymer to exert a load of about 2.0 kPa onto the ionic superabsorbent polymer.

The ionic superabsorbent polymer was allowed to absorb liquid under load for sixty minutes and then the cylindrical chamber/ionic superabsorbent polymer and liquid/fine screen assembly was removed from the Petrie dish. Any liquid clinging to the underside of the screen was removed by blotting with a paper towel and then the assembly was re-weighed to determine the amount of liquid absorbed by the ionic superabsorbent polymer under the load.

Table 1 shows the data collected for the load tests.

TABLE 1

| Weight Percent NaCl (aqueous) | Weight Percent Glycine (aqueous) | Swelling Capacity @ 2.0 kPa |
|---|---|---|
| 0.9 | 0.0 | 30.78 grams liquid/gram SAP |
| 0.9 | 4.0 | 35.78 grams liquid/gram SAP |
| 0.9 | 8.0 | 39.42 grams liquid/gram SAP |
| 1.8 | 0.0 | 24.66 grams liquid/gram SAP |
| 1.8 | 8.0 | 30.31 grams liquid/gram SAP |
| 1.8 | 12.0 | 32.09 grams liquid/gram SAP |

As the data in Table 1 indicates, testing at 0.9% (by weight) saline showed absorbency gains in the ionic superabsorbent polymer of about 25% when the swelling liquid contained 8.0% (by weight) glycine as compared to the same ionic superabsorbent polymer without any glycine. Further, testing at 1.8% (by weight) saline showed absorbency gains in the ionic superabsorbent polymer of about 23% when the swelling liquid contained 8.0% (by weight) glycine, and about 30.1% when the swelling liquid contained 12.0% (by weight) glycine, as compared to the same ionic superabsorbent polymer without any glycine.

EXAMPLE 3

In this Example, two sets of absorbent composites comprising an absorbency-enhancing additive in accordance with the present invention were prepared and tested to evaluate the increase in absorbency under a load. The first set of composites comprised pulp fibers and an ionic superabsorbent polymer. The second set of composites comprised pulp fibers, an ionic superabsorbent polymer, and glycine as an absorbency-enhancing additive.

In this Example, glycine was introduced into the ionic superabsorbent polymer as follows: glycine (250 g, Aldrich Chemical, Milwaukee, Wis.) was dissolved into water (750 g) at 60° C. and dissolved. Sodium polyacrylate ionic superabsorbent polymer (125 g, FAVOR 880, Stockhausen Inc., Greensboro, N.C.) was placed into the water/glycine mixture to create a glycine to polyacrylate ionic superabsorbent polymer weight ratio of 2:1. This resulted in a liquid to polyacrylate ionic superabsorbent polymer weight ratio of 8:1 and a water to polyacrylate ionic superabsorbent polymer weight ratio of 6:1. Once the polyacrylate ionic superabsorbent polymer imbibed all liquid, the swollen polyacrylate ionic superabsorbent polymer was spread out on a tray to a depth of about 2 cm and dried overnight in a forced air oven at 65° C. After drying, the glycine was located within the matrix of the polyacrylate ionic superabsorbent polymer.

Absorbent composites comprising solely fluff fiber (CR 1654, U.S. Alliance, Childersburg, Ala.) and ionic superabsorbent polymer (no glycine) were comprised of 40% (by weight) polyacrylate ionic superabsorbent polymer and 60% (by weight) fluff fiber. Composites comprising fluff fiber and ionic superabsorbent polymer containing glycine for testing were comprised of 40% (by weight) actual polyacrylate ionic superabsorbent polymer (not counting any weight of the glycine in the polymer matrix) and 60% (by weight) fluff fiber. Because glycine dissolves into the liquid and ultimately becomes part of the insulting liquid, the weight of glycine was not considered in specifying composite composition. Composites were compressed to a thickness of about 3.5 mm and to a density of about 0.2 g/cm³. Composites were formed into 7.6 cm diameter disks and subsequently tested for retention of liquid under load.

Each 3 inch composite disk was insulted with saline (33 mL of 0.9% by weight). Because the composite disk was comprised of about 1.277 g of actual polyacrylate ionic superabsorbent polymer, the 33 mL insult results in a liquid-loading of about 25.84 g of liquid/gram of superabsorbent, which is below the 0.3 p.s.i. (2.07 kPa) Absorbency Under Load (AUL) value for FAVOR 880 of 30 g of liquid/gram of superabsorbent. After allowing for a 60 minute equilibration period, paper blotting disks, which had been previously weighed, were then placed above and below the composite (about 4 to 7 on each side of the disk). After the blotting disks were aligned, a plain square flat plate was placed on top of the sandwich of composite and blotting disks. Finally, weights of the appropriate size to generate the desired amount of load were set on top of the blotting disks and composite. The loads used in this Example were 0.3 p.s.i. (2.07 kPa), 0.6 p.s.i. (4.14 kPa), 0.9 p.s.i. (6.21 kPa), and 1.2 p.s.i (8.28 kPa).

The blotting paper disks were allowed to absorb liquid from the composite over a period of about 2 minutes after which the blotting disks were removed from the assembly for weighing. After weighing, the amount of liquid absorbed by the blotting paper was determined by subtracting the dry weight of the blotting paper from the weight of the blotting paper after absorbing liquid. This amount of liquid was subtracted from the initial insult of 33 g to determine the amount of liquid held by the composite. The amount of liquid held by the composite was then divided by the weight of ionic superabsorbent polymer utilized resulting in a normalized value. Results from this Example are shown in FIG. 2.

Figure 2:
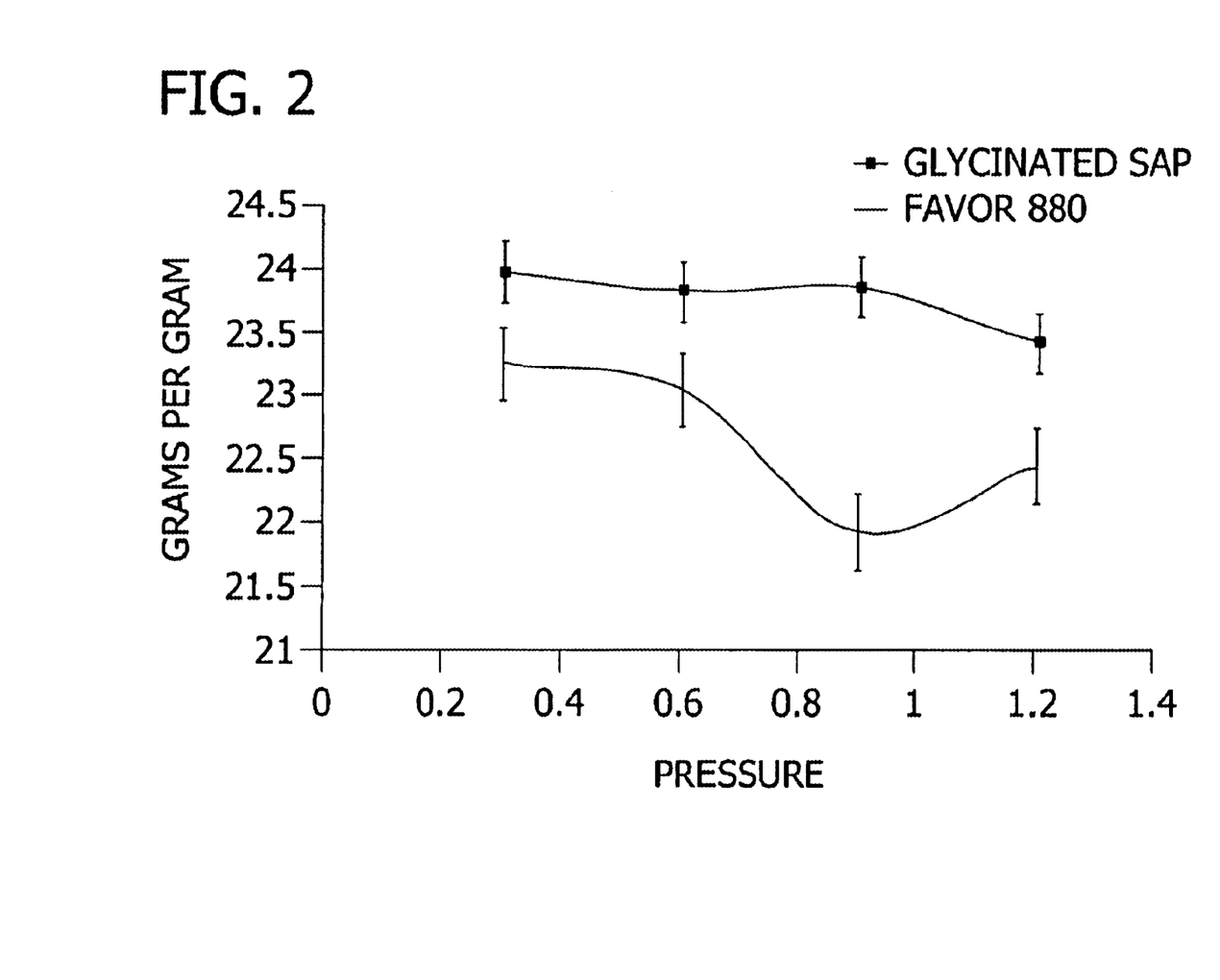
FIG. 2 is a graph showing the absorbent capacity of glycinated and non-glycinated ionic superabsorbent polymers under various loads.

As FIG. 2 indicates, the composites comprising the ionic superabsorbent polymer containing the glycine have improved retention capacity as compared to the composites lacking the glycine. The improvement in retention capacity ranges from about 2% to about 9% depending upon the load. Although these increases are lower than the increases in absorbent capacity under load discussed in Example 2, they are statistically significant.

The gains in absorbent capacity of the composites in this Example may not have been as high as those shown in Example 2 potentially due to some absorption of part of the liquid by the fluff fibers of the composite, which are known to absorb liquid and swell to a maximum of about 2 g of liquid/g of fluff fiber. Since each disk of composite material comprised about 1.915 g of fluff fiber, it would be expected that the absorption of the liquid by the fluff fiber could lead to an actual ionic superabsorbent polymer absorption level that is nearly 4.0 g of liquid/g of superabsorbent lower than the value indicated in FIG. 2. Such fluid distribution between the fluff fiber and the ionic superabsorbent polymer would lead to an improvement of over 11% for the glycinated ionic superabsorbent polymer over the non-glycinated ionic superabsorbent polymer.

EXAMPLE 4

In this Example, the effect of incorporating glycine onto an ionic superabsorbent polymer on the swelling of the ionic superabsorbent polymer in the presence of swine blood was evaluated. Glycine was incorporated onto the ionic superabsorbent polymer utilizing two separate methods.

In the first method of glycinating the ionic superabsorbent polymer, an aqueous solution of glycine was prepared by dissolving glycine (4.0 g) into water (40 mL). This 40 mL solution was sprayed over a period of time of several hours onto a sodium polyacrylate ionic polymer (FAVOR 880, Stockhausen, Inc., Greensboro, N.C.) which was spread thinly in a flat container. The polymer was allowed to dry in ambient conditions for 48 hours, and then was transferred to a convection oven held at 80° C. for 2 hours. This produced a glycine coated ionic superabsorbent polymer.

In the second method of glycinating the ionic superabsorbent polymer, a fluidized bed reactor was utilized wherein FAVOR 880 granules were suspended by air while an 18% (by weight) glycine/water solution was introduced over the granules as a fine spray. During the spraying of the glycine-containing solution, air at about 93° C. was passed through the reactor to evaporate the water in the fine spray and cause a coating to built up on the outside of the ionic superabsorbent granules until the glycine to FAVOR 880 weight ratio was about 2:1. When this ratio was achieved, the spraying was discontinued and the particles recovered for use.

The glycine polyacrylate ionic superabsorbent polymers described above were evaluated for swelling capacity in 35% HCT swine blood (Cocalico Biological Inc., Reamstown, N.J.) using a screen testing procedure with two different amounts of ionic polymer (40 mg and 400 mg). Also, untreated FAVOR 880 was tested for comparison purposes. Further, for comparison purposes to the FAVOR 880 glycinated in the fluidized bed reactor, a third FAVOR 880 superabsorbent polymer was tested. This third FAVOR 880 sample was prepared identically to the glycinated FAVOR 880 sample prepared in the fluidized bed reactor treatment with the exception that the fine spray did not contain any glycine. This sample was analyzed to determine whether the fluidized bed reactor itself changed the characteristics of the FAVOR 880. The ionic superabsorbent polymers tested in this Example were prepared such that their resulting diameter of the granules was from about 300 to about 600 µm.

An open-top ring assembly having a diameter of about 50 mm and a depth of about 3 cm containing as a bottom a 160 µm diameter screen along with a 210 µm diameter screen on top of the 160 µm diameter screen was weighed. After weighing, the upper 210 µm diameter screen was removed and the ionic superabsorbent polymer was introduced onto the 160 µm diameter screen and the 210 µm screen placed on top of the ionic superabsorbent polymer such that the ionic superabsorbent polymer was "sandwiched" between the screens in the ring assembly. Because of the size of the ionic superabsorbent polymer granules, the screens were able to keep the polymer granules from escaping.

For the 40 mg polymer tests, 10 mL of blood was introduced into an appropriately sized Petrie dish and the ring assembly, two screens, and ionic superabsorbent polymer set down into the dish such that the ionic superabsorbent polymer could absorb blood from the bottom of the dish through the 160 µm screen. An additional 10 mL of blood was then introduced on top of the ionic superabsorbent polymer through the 210 µm screen such that the ionic superabsorbent polymer could absorb blood from the top. (For the 400 mg tests, 15 mL of blood was introduced into the Petrie dish and 15 mL of blood was introduced on top of the 210 µm screen). The ionic superabsorbent polymer was allowed to absorb the blood for 30 minutes after which the assembly was removed from the Petrie dish and centrifuged at 1250 rpm to remove any blood not absorbed by the ionic superabsorbent polymer. This level of centrifugation allowed un-absorbed blood to be spun off of the assembly but was not sufficient to spin off any blood absorbed by the ionic superabsorbent polymer. The assembly was then re-weighed to determine the amount of blood absorbed by the ionic superabsorbent polymer.

The data collected in this Example for samples coated with glycine utilizing the spray method are shown in Table 2, and the data collected for samples coated with glycine utilizing the fluidized bed apparatus are shown in Table 3.

TABLE 2

| Polymer | Absorption at 40 milligrams of Polymer | Absorption at 400 milligrams of Polymer |
| --- | --- | --- |
| FAVOR 880 | 21.4 grams of blood/gram of polymer | 15.9 grams of blood/gram of polymer |
| FAVOR 880 (Glycinated) | 28.7 grams of blood/gram of polymer | 27.1 grams of blood/gram of polymer |

TABLE 3

| Polymer | Absorption at 40 milligrams of Polymer | Absorption at 400 milligrams of polymer |
| --- | --- | --- |
| FAVOR 880 | 21.3 grams of blood/gram of polymer | 16.5 grams of blood/gram of polymer |
| FAVOR 880-CP (coated with water only) | 21.7 grams of blood/gram of polymer | 11.9 grams of blood/gram of polymer |
| FAVOR 880-CPG (Glycinated) | 30.9 grams of blood/gram of polymer | 25.36 grams of blood/gram of polymer |

Figure 3:
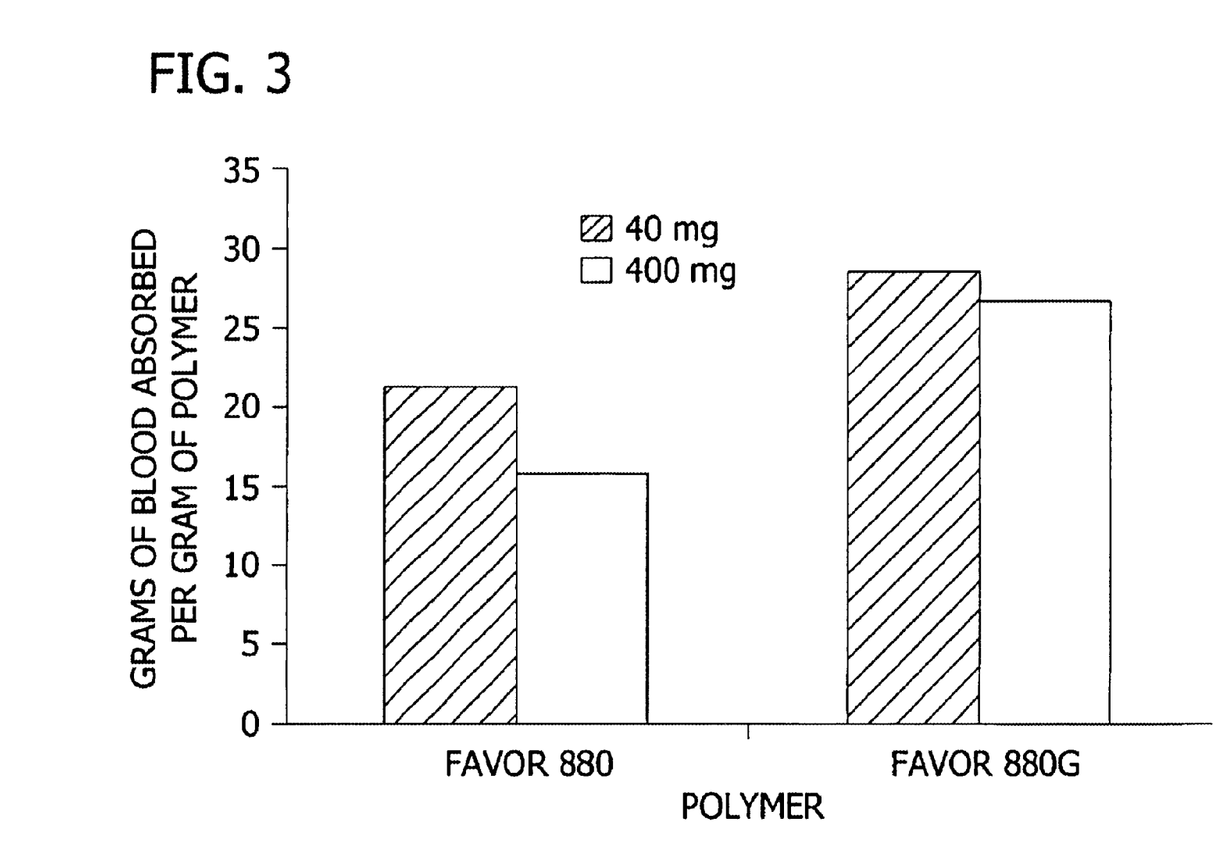
FIGS. 3 and 4 are graphs showing the effect of glycine on the swelling of an anionic superabsorbent polymer in the presence of porcine blood.

As shown in Table 2 and illustrated in FIG. 3, replicate experiments (n=4) indicated an increase in absorbent capacity of blood of about 34% at the 40 mg level and about 71% at the 400 mg level for the glycine treated superabsorbent polymers at both levels. Significantly, a substantial increase in superabsorbent capacity for glycine treated superabsorbent polymer was noted for testing done at the 400 mg level which is a replication of add-on levels of superabsorbent polymers utilized in many airformed or airlaid product composites.

Figure 4:
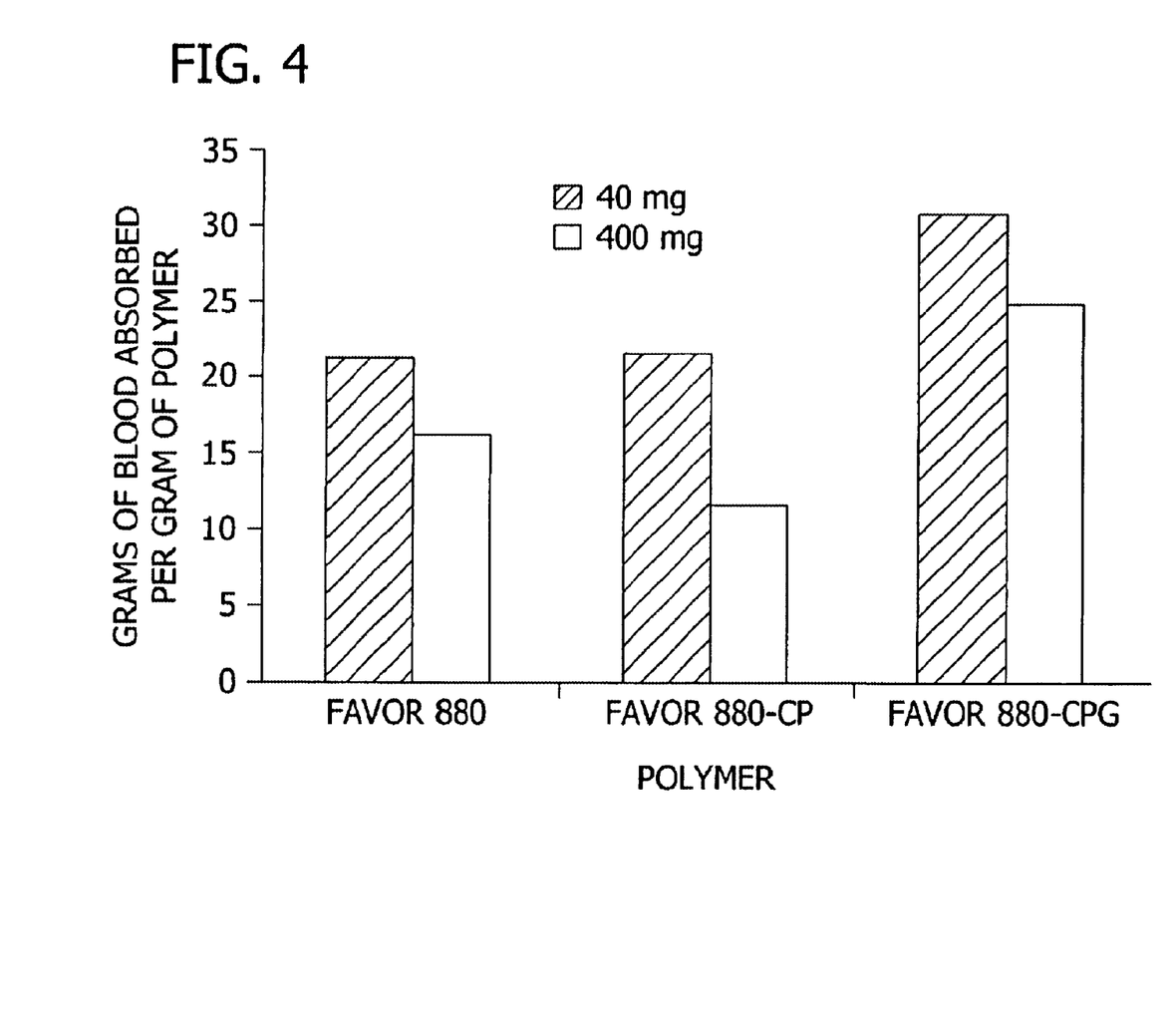

As shown in Table 3 and illustrated in FIG. 4, replicate experiments (n=4) indicated an increase in absorbent capacity of blood of about 45% at the 40 mg level and about 54% at the 400 mg level for glycine treated superabsorbent polymers at both levels.

In view of the above, it will be seen that the several objects of the invention are achieved. As various changes could be made in the above-described ionic superabsorbent polymers without departing from the scope of the invention, it is intended that all matter contained in the above description be interpreted as illustrative and not in a limiting sense.

What is claimed is:

1. An absorbent composition for absorbing an aqueous salt solution, the absorbent composition comprising an ionic superabsorbent polymer material and an absorbency-enhancing additive in a weight ratio of at least about 1:1, the additive selected from the group consisting of glycine, alpha-alanine, beat-alanine, betaine, and taurine.

2. The absorbent composition as set forth in claim 1 wherein the ionic superabsorbent polymer material comprises anionic polymer.

3. The absorbent composition as set forth in claim 2 wherein the anionic polymer is selected from the group consisting of acrylate based polymers and sulfonate based polymers.

4. The absorbent composition as set forth in claim 2 wherein the anionic polymer comprises poly(acrylic acid).

5. The absorbent composition as set forth in claim 1 wherein the ionic superabsorbent polymer material comprises a cationic polymer.

6. The absorbent composition as set forth in claim 5 wherein the cationic polymer comprises a polyamine based polymer.

7. The absorbent composition as set forth in claim 1 wherein the absorbency-enhancing additive is glycine.

8. The absorbent composition as set forth in claim 1 wherein the weight ratio of ionic superabsorbent polymer material to absorbency-enhancing additive is at least about 1:2.

9. The absorbent composition as set forth in claim 1 wherein the weight ratio of ionic superabsorbent polymer material to absorbency-enhancing additive is at least about 1:3.

10. The absorbent composition as set forth in claim 1 wherein the composition is capable of absorbing at least about 10 times its dry weight of the aqueous salt solution, the aqueous salt solution having a salt concentration of about 0.9% (by weight).

11. The absorbent composition as set forth in claim 1 wherein the absorbent composition comprises from about 5% (by weight) to about 99% (by weight) of ionic superabsorbent polymer an absorbency-enhancing additive and from about 1% (by weight) to about 95% (by weight) fluff fiber.

12. The absorbent composition as set forth in claim 1 wherein the absorbent composition is incorporated into a product selected from the group consisting of diapers, training pants, feminine napkins, interlabial pads, tampons, wound management products, and adult incontinence garments.

13. An absorbent composition for absorbing an aqueous salt solution, the absorbent composition comprising poly (acrylic acid) and an absorbency-enhancing additive, the absorbency-enhancing additive selected from the group consisting of glycine, alpha-alanine, beta-alanine, betaine, and taurine, the weight ratio of poly(acrylic acid) to absorbency-enhancing additive being at least 1:2.

14. The absorbent composition as set forth in claim 13 wherein the absorbency-enhancing additive is glycine.

15. The absorbent composition as set forth in claim 13 wherein the aqueous salt solution is selected from the group consisting of urine, blood, and menses.

16. The absorbent composition as set forth in claim 13 wherein the absorbent composition is incorporated into a product selected from the group consisting of diapers, training pants, feminine napkins, interlabial pads, tampons, wound management products, and adult incontinence garments.

17. The absorbent composition as set forth in claim 13 wherein the absorbent composition comprises from about 5% (by weight) to about 99% (by weight) of ionic superabsorbent polymer an absorbency-enhancing additive and from about 1% (by weight) 95% (by weight) fluff fiber.

18. A process for increasing the osmotic activity of an ionic superabsorbent polymer material in the presence of an aqueous salt solution, the process comprising combining an absorbency-enhancing additive with the ionic superabsorbent polymer material prior to contacting the ionic superabsorbent polymer with the aqueous salt solution, the weight ratio of the ionic superabsorbent polymer to the absorbency-enhancing additive being at least about 1:1, the additive selected form the group consisting of glycine, alpha-alanine, beta-alanine, betaine, and taurine.

19. The process as set forth in claim 18 wherein the ionic superabsorbent polymer comprises an anionic polymer.

20. The process as set forth in claim 19 wherein the ionic superabsorbent polymer is selected from the group consisting of acrylate based polymers and sulfonate based polymers.

21. The process as set forth in claim 20 wherein the ionic superabsorbent polymer comprises poly(acrylic acid).

22. The process as set forth in claim 18 wherein the ionic superabsorbent polymer comprises a cationic polymer.

23. The process as set forth in claim 22 wherein the ionic superabsorbent polymer comprises a polyamine based polymer.

24. The process as set forth in claim 18 wherein the absorbency-enhancing additive is glycine.

25. The process as set forth in claim 18 wherein the weight ratio of ionic superabsorbent polymer to absorbency-enhancing additive is at least about 1:3.

26. The process as set forth in claim 18 wherein the weight ratio of ionic superabsorbent polymer to absorbency-enhancing additive is at least about 1:4.

27. The process as set forth in claim 18 wherein the ionic superabsorbent polymer is incorporated into a product selected from the group consisting of diapers, training pants, feminine napkins, interlabial pads, tampons, wound management products and adult incontinence garments.

28. The process as set forth in claim 18 wherein the ionic polymer comprises poly(acrylic acid) and the additive comprises glycine, the weight ratio of ionic superabsorbent polymer to absorbency-enhancing additive being from about 1:1 to about 1:2.

29. The process as set forth in claim 18 wherein the additive is introduced onto the ionic superabsorbent polymer material by contacting superabsorbent polymer granules suspended in a fluidized bed with an aqueous spray containing the additive and evaporating water.

30. A composite product for absorbing an aqueous salt solution, the product comprising an absorbent composition comprising an ionic superabsorbent polymer material, fluff fiber, and an additive, the weight ratio of the ionic superabsorbent polymer to the absorbency-enhancing additive being at least 1:2, the additive selected from the group consisting of glycine, alpha-alanine, beta-alanine, betaine, and taurine.

31. The composite product as set forth in claim 30 wherein the additive is contained in or on the ionic superabsorbent polymer material.

32. The composite product composition as set forth in claim 30 wherein the additive is contained in or on the fluff fibers.

33. The process as set forth in claim 18 wherein the weight ratio of ionic superabsorbent polymer to absorbency-enhancing additive is at least about 1:2.

* * * * *

UNITED STATES PATENT AND TRADEMARK OFFICE
CERTIFICATE OF CORRECTION

| | | |
|---|---|---|
| PATENT NO. | : 6,855,434 B2 | Page 1 of 1 |
| APPLICATION NO. | : 10/084571 | |
| DATED | : February 15, 2005 | |
| INVENTOR(S) | : Alice Y. Romans-Hess and Joseph R. Feldkamp | |

It is certified that error appears in the above-identified patent and that said Letters Patent is hereby corrected as shown below:

On the front cover of the patent, section 75, Inventors: "Alice Y. Romasn-Hess" should read -- Alice Y. Romans-Hess --.

Signed and Sealed this

Seventeenth Day of April, 2007

JON W. DUDAS
*Director of the United States Patent and Trademark Office*